United States Patent [19]
Carati et al.

[11] Patent Number: 5,578,744
[45] Date of Patent: Nov. 26, 1996

[54] CATALYTICALLY ACTIVE GEL AND A PROCESS FOR ITS PREPARATION

[75] Inventors: Angela Carati, San Giuliano Milanese; Enrico Davini, Monterotondo; Mario G. Clerici, San Donato Milanese; Giuseppe Bellussi, Piacenza, all of Italy

[73] Assignees: Eniricerche S.p.A.; Snamprogetti S.p.A., both of Milan, Italy

[21] Appl. No.: 444,414

[22] Filed: May 19, 1995

Related U.S. Application Data

[62] Division of Ser. No. 134,854, Oct. 12, 1993, Pat. No. 5,434,118, which is a continuation of Ser. No. 810,497, Dec. 19, 1991, abandoned.

[30] Foreign Application Priority Data

Dec. 21, 1990 [IT] Italy ........................ 22477/90

[51] Int. Cl.$^6$ ................ C07C 2/00; C07C 2/12
[52] U.S. Cl. ................ 585/530; 549/523; 549/524; 564/298; 564/300; 564/301; 568/771
[58] Field of Search ................ 585/530; 549/523, 549/524; 564/298, 300, 301; 568/771

[56] References Cited

U.S. PATENT DOCUMENTS

| | | |
|---|---|---|
| Re. 21,690 | 1/1941 | Bond et al. ................ 252/270 |
| 1,577,186 | 3/1926 | Patrick . |
| 2,551,015 | 5/1951 | Kimberlin, Jr. et al. ................ 252/457 |
| 2,697,066 | 12/1954 | Sieg ................ 196/50 |
| 4,006,175 | 2/1977 | Termin et al. ................ 260/438 |
| 4,062,873 | 12/1977 | Harrison ................ 260/346 |
| 4,367,342 | 1/1983 | Wulff et al. ................ 549/529 |
| 4,392,990 | 7/1983 | Witt ................ 252/458 |
| 4,410,501 | 10/1983 | Taramasso et al. ................ 423/326 |
| 4,764,497 | 8/1988 | Yuasa et al. ................ 502/235 |
| 4,764,499 | 8/1988 | Vanderspurt et al. ................ 502/258 |
| 4,954,653 | 9/1990 | Bellussi et al. ................ 564/223 |
| 5,049,536 | 9/1991 | Bellussi et al. ................ 502/235 |
| 5,059,573 | 10/1991 | Sasaki et al. ................ 502/205 |
| 5,126,491 | 6/1992 | Clerici et al. ................ 568/342 |
| 5,434,118 | 7/1995 | Carati et al. ................ 502/242 |

FOREIGN PATENT DOCUMENTS

| | | |
|---|---|---|
| 560670 | 7/1958 | Canada . |
| 0067459 | 12/1982 | European Pat. Off. . |
| 0340868 | 11/1989 | European Pat. Off. . |
| 0352715 | 1/1990 | European Pat. Off. . |
| 658256 | 11/1947 | France . |

*Primary Examiner*—Asok Pal
*Attorney, Agent, or Firm*—Margaret B. Kelley, Esq.

[57] ABSTRACT

A catalytically active gel is described consisting of a silica matrix with uniform porosity, monomodal pore distribution and high surface area, within which one or metal oxides possessing catalytic activity are dispersed. A process for preparing this catalytic gel is also described.

17 Claims, No Drawings

CATALYTICALLY ACTIVE GEL AND A PROCESS FOR ITS PREPARATION

This is a division of application Ser. No. 08/134,854, filed Oct. 12, 1993, now U.S. Pat. No. 5,434,118 which is a continuation of application Ser. No. 07/810,497 filed Dec. 19, 1991, now abandoned.

This invention relates to a catalytically active gel consisting of a silica matrix within which one or more metal oxides possessing catalytic activity are dispersed. The invention also relates to the use of this gel as a catalyst.

Certain amorphous silica-alumina gels possessing catalytic activity are known in the art. For example, European patent application 160,145 describes an aromatic hydrocarbon alkylation method using an amorphous silica-alumina gel catalyst with a mean pore diameter typically of between 50 and 500 Å and a silica/alumina ratio typically of between 1/1 and 10/1. M. R. S. Manton and J. C. Davidtz in Journal of Catalysis, 60, pp 156–166 (1979) describe a process for the synthesis of amorphous silica-alumina catalysts with a controlled pore volume. These catalysts possess pores with a diameter typically of between 3.7 and 15 nm (37–150 Å).

Italian patent 1,219,692 describes a silica-alumina gel which is amorphous to X-rays, is microporous and is catalytically active. A gel possessing catalytic activity has now been discovered consisting of a silica matrix within which one or more metal oxides are uniformly dispersed, and having monomodal porosity in the micropore region (diameter of the order of 10 Å), the gel exhibiting its catalytic activity in different types of reaction according to the various oxides contained in it, but mainly in oxidation reactions and acid-catalyzed reactions.

In accordance therewith, the present invention provides an X-ray amorphous gel:

possessing catalytic activity in acid-catalyzed or oxidation reactions;

consisting of a silica matrix within which one or more metal oxides exhibiting catalytic activity are uniformly dispersed, these being chosen from: titanium, gallium, chromium, iron, zirconium, vanadium, molybdenum, zinc, cobalt, phosphorus and tin;

having monomodal porosity in the micropore region and a large surface area, characterised by a molar $SiO_2$/metal oxide ratio of between 5/1 and 300/1, said gel being obtained by:

a) preparing an aqueous solution of:

1) a tetra alkyl ammonium hydroxide (TAA-OH) in which the alkyl is chosen from ethyl, n-propyl and n-butyl;

2) a soluble silicon compound able to hydrolyze into $SiO_2$;

3) one or more soluble salts or acids of one or more metals, the oxides of which exhibit catalytic activity;

the quantity of solution constituents being such as to respect the following molar ratios:

| | |
|---|---|
| $SiO_2$/metal oxides | between 5/1 and 300/1 |
| TAA-OH/$SiO_2$ | between 0.05/1 and 0.5/1 |
| $H_2O$/$SiO_2$ | between 5/1 and 40/1; | b) heating the solution thus obtained to cause gelling;

c) drying the gel;

d) calcining the dried gel, operating firstly in an inert atmosphere and then in an oxidizing atmosphere.

The use of tetra ethyl, n-propyl or n-butyl ammonium hydroxide in stage a) of the process is critical. In this respect, the use of similar ammonium compounds such as tetra methylammonium hydroxide leads to the formation of gels possessing mesopores. The soluble silicon compounds used in stage a) of the process are preferably tetraalkyl silicates such as tetraethyl silicate.

The water-soluble salts or acids of one or more metals the oxides of which exhibit catalytic activity, particularly of acid and oxidative catalysis type, are chosen from the more water-soluble or hydrolyzable salts or acids of the metals concerned.

Stage a) of the process is conducted at ambient temperature (20°–25° C.) or at higher than ambient temperature up to that approaching the gel initiation temperature (about 50° C.).

The order in which the solution constituents are added in stage a) is not critical. It is however preferable to firstly form an aqueous solution containing the tetra alkyl ammonium hydroxide and the soluble compound of the metals the oxides of which exhibit catalytic activity, and then to add the soluble silicon compound to this solution.

Water-alcohol solutions of the solution components can also be used in stage a).

In all cases the following molar ratios must be respected in the resultant solution:

| | |
|---|---|
| $SiO_2$/metal oxides | between 5/1 and 300/1 |
| TAA-OH/$SiO_2$ | between 0.05/1 and 0.5/1 |
| $H_2O$/$SiO_2$ | between 5/1 and 40/1; |

The preferred values for these ratios are:

| | |
|---|---|
| $SiO_2$/metal oxides | between 10/1 and 200/1 |
| TAA-OH/$SiO_2$ | between 0.1/1 and 0.3/1 |
| $H_2O$/$SiO_2$ | between 10/1 and 25/1. |

The gelling in stage b) of the process is achieved by heating the solution to a temperature in the range of 50°–70° C. and preferably of the order of 60° C. The time for complete gelling varies according to the temperature, the concentrations and other factors, it being normally between 15 minutes and 5 hours, and typically of the order of 25–60 minutes. It is essential that gelling be effected by simply heating the solution. In this respect, if gelling is effected under acid conditions as in the known art, a gel is obtained having undesirable characteristics, especially in relation to porosity and the pore size distribution. The gel obtained in this manner is dried in stage c) of the process of the present invention. This drying is conveniently conducted at a temperature of up to 150° C. and preferably of the order of 90°–100° C., for a time sufficiently long to eliminate water completely or substantially completely. In one embodiment of the process of the present invention, the drying in stage c) is effected by spray drying. In this case a spray drier can be used into which the gel is injected in the form of droplets which come into contact with an inert gas, operating with a gas inlet temperature of the order of 230°–250° C. and an outlet temperature of the order of 140°–160° C.

In all cases the gel is calcined in stage d) of the process of the present invention, this calcining being conveniently conducted firstly in an inert atmosphere such as nitrogen, and then in an oxidizing atmosphere such as air. The calcining temperature is conveniently within the range of 500°–700° C. and preferably of the order of 500°–600° C. The calcining time can vary from 4 to 20 hours and is typically of the order of 6–16 hours.

In this manner the catalytically active silica gel of the present invention is obtained with a structure completely amorphous to X-rays and is characterised by an SiO$_2$/metal oxide ratio equivalent to that deriving from the initially fed silicon and other metal compounds and being between 5/1 and 300/1, and preferably between 10/1 and 200/1.

This metal-silica gel has a large surface area of between 560 and 1000 m$^2$/g (BET determination). The total pore volume is between 0.3 and 0.6 ml/g. The pores are within the micropore range with a mean diameter of the order of 10 Å or less and with a narrow size distribution. In particular, pores with a diameter exceeding 30 Å are absent or virtually absent, and pores with a diameter exceeding 20 Å are generally absent.

The metal-silica gel of the present invention is catalytically active, the type of catalytic activity depending on the type of oxides incorporated. For example, metal-silica gels containing one or more metal oxides chosen from molybdenum, titanium and vanadium are active in the epoxidation of olefins to cycloolefins. Metal-silica gels containing molybdenum and vanadium are equally active in the oxidation of amines to oximes, and metal-silica gels containing gallium or iron are active in the oligomerization of olefins.

Metal-silica gels containing zirconium, molybdenum, vanadium or chromium or their mixtures are preferably active in the hydroxylation of phenol to pyrocatechol and hydroquinone.

The following experimental examples are given to better illustrate the present invention.

EXAMPLE 1

Gallium silica gel 38 g of a 30 wt % aqueous solution of tetrapropyl ammonium hydroxide are placed in a 400 cc pyrex glass beaker provided with a magnetic stirrer and supported on an agitating and heating plate.

This solution is diluted with a further 26.7 cc of water, and 1.33 g of Ga(NO$_3$)$_3$.8H$_2$O are added.

The mixture is then heated to about 55° C., and 34.7 g of tetraethylsilicate are added to the clear hot solution. The mixture is left under agitation until the system gels, generally about one hour after the ethylsilicate addition, to produce a perfectly clear compact gel which can no longer be agitated. The gel is then left to age for 48 hours at ambient temperature, and is then placed in a 1 liter flask on a rotary evaporator.

The evaporator thermostatic bath temperature is adjusted to about 90° C., the flask is rotated at maximum speed and a light air flow is fed over the sample to facilitate drying at atmospheric pressure. These conditions are maintained for 3–4 hours. The discharged sample is then placed in an oven for 1 hour at 100° C. A dry gel is obtained in this manner and is then calcined for three hours in nitrogen at 550° C. (to eliminate most of the organic material trapped within the solid by pyrolysis), and then for 10 hours in air at 600° C. to burn off the unburnt carbon residues. 11.2 g of gallium silica gel are obtained having the following characteristics:

surface area: 823 m$^2$/g pore volume: 0.32 cm$^3$/g

The mean pore diameter (B.E.T) is of the order of 10 Å or less, and pores with a diameter exceeding 20 Å are absent.

EXAMPLE 2

Tin silica gel

A tin silica gel is prepared (32.3 g) from an aqueous solution consisting of 148.3 g of water, 31.3 g of tetrapropyl ammonium hydroxide and 4 g of (NH$_4$)$_2$SnCl$_6$ to which 104.1 g of tetraethylsilicate are then added. The procedure used is as described for Example 1.

EXAMPLE 3

Titanium silica gel

A titanium silica gel is prepared in the following manner:

A mixture consisting of 104.1 g of tetraethylsilicate and 4.5 g of tetraethylorthotitanate is added to an aqueous solution containing 103.8 g of water and 31.3 g of tetrapropyl ammonium hydroxide. After about 2 hours a homogeneous transparent yellow gel forms. It is dried in a rotary evaporator at 100° C. under a nitrogen flow. It is then calcined at 550° C. for 1 hour in nitrogen and for 10 hours in air. 31.9 g of gel are obtained.

EXAMPLE 4

Vanadium silica gel

A vanadium silica gel (32.1 g) is prepared by adding to a solution containing 53 g of tetrapropyl ammonium hydroxide (29.89% titre) and 55 g of water a second solution containing 2.3 g of NH$_4$VO$_3$ and 104 g of tetraethyl orthosilicate. The procedure is described in Example 1.

EXAMPLE 5

Chromium silica gel

Following the procedure described in Example 1, 33.3 g of chromium silica gel are prepared by adding to a mixture consisting of 73 g of tetrapropyl ammonium hydroxide (29.89% titre) and 55 g of water a second mixture consisting of 4 g of Cr(NO$_3$)$_3$.9H$_2$O, 50 g of ethanol and 104 g of tetraethylsilicate.

EXAMPLE 6

Iron silica gel

This gel (31.8 g) was prepared following the procedure described in Example 1 from a solution containing 73 g of tetrapropyl ammonium hydroxide (29.89% titre) and 55 g of water, to which a second solution containing 50 g of ethanol, 4 g of Fe(NO$_3$)$_3$.9H$_2$O and 104 g of tetraethylsilicate is added.

EXAMPLE 7

Zirconium silica gel

This gel (34.0 g) was prepared following the procedure described in Example 1 from a solution containing 50 g of water and 85 g of tetrapropyl ammonium hydroxide (29.89% titre), which was added to a second solution containing 6.5 g of Zr(OC$_3$H$_7$)$_4$ and 104 g of tetraethylsilicate.

EXAMPLE 8

Molybdenum silica gel

This gel (35.8 g) was prepared from a solution containing 53 g of tetrapropyl ammonium hydroxide (28.89% titre) and 3.4 g of molybdic acid, which was added to a second solution containing 55 g of water and 104 g of tetraethylsilicate.

EXAMPLE 9

Zinc silica gel 104 g of tetraethylsilicate and then 2.7 g of ZnCl$_2$ in 50 g of ethanol are added to a solution of 70 g of tetrapropyl ammonium hydroxide (29.89% titre) in 30 g of water. After following the procedure described in Example 1, 34.3 g of zinc silica gel are obtained.

EXAMPLE 10

Cobalt silica gel 81 g of tetrapropyl ammonium hydroxide (29.89% titre) are added to a solution of 5.8 g of $Co(NO_3)_2.6H_2O$ in 30 g of water; air of chromatographic purity washed in 3M NaOH for 24 hours is bubbled through very slowly. 104 g of tetraethylsilicate are then added and the procedure described in Example 1 is then followed to finally obtain 30.6 g of cobalt silica gel.

EXAMPLE 11

Titaniumlmolybdenum silica gel

A solution containing 3.4 g of molybdic acid, 80 g of tetrapropyl ammonium hydroxide (28% titre) and 60 g of water is prepared. 104 g of tetraethylsilicate and 4.5 g of tetraethyl ortho titanate are then added to this solution. Proceding as described in Example 1, 35.7 g of Titanium/molybdenum silica gel are obtained.

EXAMPLE 12

Phosphorus/vanadium silica gel

A solution containing 70 g of tetrapropyl ammonium hydroxide (28% titre), 2.9 g of 85% phosphoric acid and 2.3 g of $NH_4\ VO_3$ is prepared. 38 g of water and 104 g of tetraethylsilicate are then added to this solution. Proceding as described in Example 1, 32.58 g of phosphorus/vanadium silica gel are obtained with a surface area of 603 $m^2/g$.

EXAMPLE 13

Iron/titanium silica gel

A solution containing 75 g of tetrapropyl ammonium hydroxide (28% titre) and 55 g of water is prepared. 104 g of tetraethylsilicate, 4.5 g of tetraethyl orthotitanate and a solution of 4 g of $Fe(NO_3)_3.9H_2O$ in 50 g of ethanol are added. Proceding as described in Example 1, 32.3 g of Iron/titanium silica gel are obtained.

EXAMPLE 14

Catalytic activity of Molybdenum silica gel

The catalytic activity of the molybdenum silica gel prepared as described in Example 8 is examined in this example in relation to the epoxidation of various olefins with tert-butyl hydroperoxide (TBHP) and to the oxidation of cyclohexylamine to cyclohexyloxime with hydrogen peroxide and TBHP.

EXAMPLE 14a

Epoxidation of cyclohexene 810 mg of cyclohexene (9.88 mmoles) and 40 mg of molybdenum silica gel are weighed into a bottle with a screw stopper provided with a perforable rubber diaphragm. The bottle, provided with a magnetic anchor stirrer, is closed and placed in a drilled aluminium block. The block is heated to 85° C. and after 30 minutes 1.41 g (12.5 mmoles) of TBHP of 80% concentration are added with a syringe. The progress of the reaction is followed by gas chromatographic analysis with an internal standard. The following results are obtained:

|  | Conversion | Selectivity |
|---|---|---|
| After 18 hours at 25° C.: | | |
| cyclohexene | 30.2% | 100% |
| TBHP | 30.9% | 77% |
| After 18 hours at 60° C.: | | |
| cyclohexene | 45.0% | 100% |
| TBHP | 57.7% | 62% |
| After 18 hours at 85° C.: | | |
| cyclohexene | 71.3% | 100% |
| TBHP | 95.0% | 58% |

EXAMPLE 14b

Epoxidation of 1-octene

Using the procedure described in Example 14a, 40 mg of molybdenum silica gel, 730 mg (6.51 mmoles) of 1-octene and 90 mg (0.8 mmoles) of TBHP of 80% concentration are fed. After one hour at 100°–110° C. the TBHP conversion is 69.2% and its selectivity 13.4%, the epoxide yield and selectivity being 9.3%.

EXAMPLE 14c

Epoxidation of 2-cyclohexen-1-ol

Using the procedure described in Example 14a, 40 mg of molybdenum silica gel, 1.0 g (10.2 mmoles) of 2-cyclohexen-1-ol and 1.18 g (10.5 mmoles) of TBHP of 80% concentration are fed.

After 2 hours at 80° C. the olefin conversion is 66%, the epoxide yield is 82%, the TBHP conversion is 60% and its selectivity is 87%.

EXAMPLE 14d

Oxidation of cyclohexylamine with TBHP 860 mg (8.24 mmoles) of cyclohexylamine, 40 mg of catalyst and 1.07 g of 80% TBHP are fed into a flask. After 2 hours at 80° C. the TBHP conversion is 64%, the cyclohexylamine conversion is 30% and the oxime yield is 5%.

EXAMPLE 14e

Oxidation of cyclohexylamine with hydrogen peroxide 860 mg (8.24 mmoles) of cyclohexylamine, 1.6 ml of 30% $H_2O_2$ (16.48 mmoles) and 40 mg of catalyst are fed into a flask. After 2 hours at 85° C. the amine conversion is 16%, the oxime yield is 8% and the oxime selectivity with respect to the substrate is 50%.

EXAMPLE 14f

Hydroxylation of phenol 25 g of phenol, 2.5 ml of water and 0.3 g of catalyst are fed into a flask. The suspension is heated to 100° C. under stirring. 6 ml of 33% $H_2O_2$ are then slowly added to it dropwise. On termination of the reaction the catalyst is separated and the reaction products are analyzed by gas chromatography.

After 30 minutes at this temperature, the $H_2O_2$ conversion is 100%, the pyrocatechol+hydroquinone yield being 19%.

EXAMPLE 15

Catalytic activity of Vanadium silica gel

The catalytic activity of the vanadium silica gel prepared as described in Example 4 is examined in this example in relation to the epoxidation of various olefins and the hydroxylation of phenols.

EXAMPLE 15a

Epoxidation of cyclohexene

Using the procedure described in Example 14a, 810 mg of cyclohexene (9.88 mmoles), 40 mg of vanadium silica gel and 1.41 g (12.5 mmoles) of 80% TBHP are fed. The following results are obtained:

|  | Conversion | Selectivity |
|---|---|---|
| After 18 hours at 25° C.: |  |  |
| cyclohexene | 4.1% | 100% |
| TBHP | 13.3% | 24% |
| After 18 hours at 60° C.: |  |  |
| cyclohexene | 44.1% | 100% |
| TBHP | 52.0% | 68% |
| After 18 hours at 85° C.: |  |  |
| cyclohexene | 57.0% | 100% |
| TBHP | 65.3% | 68% |

EXAMPLE 15b

Epoxidation of 1-octene

Using the procedure described in Example 14a, 40 mg of vanadium silica gel, 730 mg (6.51 mmoles) of 1-octene and 90 mg (0.8 mmoles) of TBHP of 80% concentration are fed. After one hour at 100°–110° C. the TBHP conversion is 36% and its selectivity is 86%.

EXAMPLE 15c

Hydroxylation of phenol 25 g of phenol, 2.5 ml of $H_2O$ and 0.3 g of catalyst are fed into a flask. The suspension is heated to 100° C. under stirring. 6 ml of 33% w/v $H_2O_2$ are then slowly added to it dropwise. On termination of the reaction the catalyst is separated and the reaction products are analyzed by gas chromatography using a column of length 6 feet filled with 10% SP 2250.

After 150 minutes at this temperature, the $H_2O_2$ conversion is 11%, the pyrocatechol+hydroquinone yield being 20%.

EXAMPLE 15d

Oxidation of cyclohexylamine with TBHP 860 mg (8.24 mmoles) of cyclohexylamine, 40 mg of catalyst and 1.07 g (9.52 mmoles) of 80% TBHP are fed into a flask. After 2 hours at 80° C. the TBHP conversion is 78%, the cyclohexylamine conversion is 16% and the oxime yield is 2%.

EXAMPLE 16

Catalytic activity of Titanium silica gel

EXAMPLE 16a

Epoxidation of 1-octene

Using the procedure described in Example 15a, 15.2 mmoles of 1octene, 50 mg of titanium silica gel prepared as described in Example 3, and 2.5 mmoles of 80% TBHP are fed. After one hour at 110° C. the 1-octene conversion is 3.9%, the TBHP conversion is 27% and the TBHP selectivity is 87%.

If 33 mmoles of 1-octene, 5 moles of 80% TBHP and 15 mg of catalyst are fed instead, after 240 minutes at 110° C. the 1-octene conversion is 2.4%, the TBHP conversion is 26% and the TBHP selectivity is 60%.

EXAMPLE 17

Activity of Titanium/molybdenum silica gel

EXAMPLE 17a

Epoxidation of cyclohexene

Using the procedure described in Example 15a, 9.88 mmoles of cyclohexene, 40 mg of titanium/molybdenum silica gel prepared as described in Example 11 and 12.5 mmoles of 80% TBHP are fed. After 18 hours at 85° C., the cyclohexene conversion is 58%, its selectivity 100%, the TBHP conversion is 61% and its selectivity 95%.

EXAMPLE 17b

Epoxidation of 1-octene

Using the procedure described in Example 15a, 6.5 mmoles of 1-octene, 0.8 mmoles of 80% TBHP and 40 mg of titanium/molybdenum silica gel are fed. After one hour at 110° C. the 1-octene conversion is 39.9%, the TBHP conversion is 47.6% and the TBHP selectivity is 83.8%.

EXAMPLE 18

Activity of Gallium silica gel

EXAMPLE 18a

Oligomerization of 1-octene 6 ml of anhydrous 1-octene and 0.4 g of catalyst (prepared as described in Example 1) previously dried at 400° C. for 3 hours are fed into a glass pressure vessel of about 30 ml capacity provided with a thermocouple well. The suspension is heated to a temperature of 150° C. for 3 hours. After cooling, the catalyst is separated and the reaction products analyzed by gas chromatography in a column of length 4 feet filled with 3% SP 2100 (5 minutes to 100° C. and then to 280° C. at a rate of 25° C./min): the octene represents 57.1% (in % of gas chromatographic area); the dimers represent 33.4%; the trimers represent 6.9% and the tetramers represent 2.6%.

EXAMPLE 18b

Alkylation of benzene

Proceeding as described in Example 18a, 1.45 g of 1-octene, 10 cc of benzene and 0.0378 g of n-decane as internal gas chromatography standard are fed.

After 3 hours at 150° C., the residual octene is 9.69 mmoles, the alkylates being 3.20 mmoles.

EXAMPLE 19

Activity of Iron silica gel

EXAMPLE 19a

Oligomerization of 1-octene

Proceeding as described in Example 18a, 6 ml of anhydrous 1-octene and 0.4 g of catalyst prepared as described in Example 6 are fed.

After 3 hours at 200° C., the octene represents 91.0% (in % of gas chromatographic area) and the dimers represent 9.0%.

EXAMPLE 19b

Alkylation of benzene

Proceeding as described in Example 18a, 1.45 g of 1-octene, 10 cc of benzene and 0.0370 g of n-decane as internal gas chromatography standard are fed. After 3 hours at 150° C., the residual octene is 12.54 mmoles, the alkylates being 0.41 mmoles.

EXAMPLE 20

Activity of Zirconium silica gel in hydroxylation of phenol

Proceeding as described in Example 15c and using the catalyst prepared as in Example 7, after 3 hours at 100° C. the $H_2O_2$ conversion is 66% and the pyrocatechol+hydroquinone yield is 19%.

EXAMPLE 21

Activity of Chromium silica gel

Proceeding as described in Example 15c and using the catalyst prepared as in Example 5, after 2 hours at 100° C. the $H_2O_2$ conversion is 100% and the pyrocatechol+hydroquinone yield is 25%.

We claim:

1. A catalytic process, which is carried out in the presence of a gel product which is amorphous to X-rays and catalytically active in acid-catalyzed or oxidation reactions and which consists of a silica matrix within which one or more oxides exhibiting catalytic activity are uniformly dispersed; which gel product has a monomodal porosity in the micropore region and a large surface area and has a molar ratio $SiO_2$ to catalytic oxide of between 5/1 and 300/1; the gel product being prepared by:

a) preparing an aqueous solution of (1) a tetra-alkyl ammonium hydroxide (TAA-OH) where the alkyl group is ethyl, n-propyl or n-butyl; (2) a water-soluble silicon compound which is hydrolyzable to $SiO_2$; (3) one or more water-soluble salts and acids which form the catalytic oxides and which are water-soluble salts and acids of elements selected from the group consisting of titanium, gallium, chromium, iron, zirconium, vanadium, molybdenum, zinc, cobalt, phophorous and tin;

with the quantity of solution constituents being within the following molar ratios:

| | |
|---|---|
| $SiO_2$/catalytic oxides | between 5/1 and 300/1, |
| TAA—OH/$SiO_2$ | between 0.05/1 and 0.5/1, and |
| $H_2O$/$SiO_2$ | between 5/1 and 40/1; | b) heating the solution to cause gelling;
    c) drying the gel; and
    d) calcining the dried gel, first in an inert atmosphere and then in an oxidizing atmosphere.

2. The catalytic process of claim 1, wherein the soluble silicon compound is tetraethyl silicate.

3. The catalytic process of claim 1, wherein the oxide is a titanium oxide.

4. The catalytic process of claim 1, wherein the process is an olefin epoxidation.

5. The catalytic process of claim 1, wherein the process is a cyclolefin epoxidation.

6. The catalytic process of claim 1, wherein the process is an amine oxidation.

7. The catalytic process of claim 1, wherein the process is an olefin oligomerization.

8. The catalytic process of claim 1, wherein the process is a phenol hydroxylation.

9. The catalytic process of claim 1, wherein in step a) the solution constituents are present in quantities within the range of the following molar ratios:

| | |
|---|---|
| $SiO_2$/catalytic oxides | between 10/1 and 200/1 |
| TAA-OH/$SiO_2$ | between 0.1/1 and 0.3/1 |
| $H_2O$/$SiO_2$ | between 10/1 and 25/1 |

10. The catalytic process of claim 1, wherein in step a) the preparation is conducted at a temperature of about 20° C. to about 50° C.

11. The catalytic process of claim 1, wherein in step b) the gelling is effected at a temperature of between 50° and 70° C. for a time of between 15 minutes to 5 hours.

12. The catalytic process of claim 11, wherein the gelling is effected at a temperature of 60° C. for a time of the order of 25–60 minutes.

13. The catalytic process of claim 1, wherein in step c) the drying is effected at a temperature of up to 150° C.

14. The catalytic process of claim 13, wherein the drying is effected at a temperature of the order of 90°–100° C.

15. The catalytic process of claim 14, wherein the drying stage is effected by spray drying.

16. The catalytic process of claim 1, wherein in step d) the calcining is effected at a temperature of between 500° and 700° C. for a time of between 4 and 20 hours.

17. The catalytic process of claim 16, wherein the calcining is effected at about 550°–600° C. for about 6–16 hours.

* * * * *